United States Patent
Mochizuki et al.

(10) Patent No.: US 6,602,513 B2
(45) Date of Patent: *Aug. 5, 2003

(54) FACE PACK

(75) Inventors: Miyoko Mochizuki, Yokohama (JP); Masaaki Ishiwatari, Yokohama (JP); Miharu Nishida, Yokohama (JP)

(73) Assignee: Shiseido Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/331,897

(22) PCT Filed: Nov. 25, 1998

(86) PCT No.: PCT/JP98/05305

§ 371 (c)(1), (2), (4) Date: Jul. 9, 1999

(87) PCT Pub. No.: WO99/27898

PCT Pub. Date: Jun. 10, 1999

(65) Prior Publication Data

US 2002/0018793 A1 Feb. 14, 2002

(30) Foreign Application Priority Data

Nov. 27, 1997 (JP) .............................................. 9-342189

(51) Int. Cl.$^7$ ............................ A61K 7/00; A61K 31/74
(52) U.S. Cl. .................. 424/401; 424/78.02; 424/78.03; 424/489
(58) Field of Search ........................... 424/78.02, 78.03, 424/489, 400, 401

(56) References Cited

U.S. PATENT DOCUMENTS

| | | | | |
|---|---|---|---|---|
| 4,126,142 A | * | 11/1978 | Saute | 424/400 |
| 5,534,265 A | * | 7/1996 | Fowler et al. | 424/489 |
| 5,683,706 A | * | 11/1997 | LaFleur et al. | 424/401 |

FOREIGN PATENT DOCUMENTS

| | | |
|---|---|---|
| JP | 58180408 | 10/1983 |
| JP | 58216109 | 12/1983 |
| JP | 60165902 | 8/1985 |
| JP | 02145505 | 6/1990 |

* cited by examiner

Primary Examiner—Thurman K. Page
Assistant Examiner—Rachel M. Bennett
(74) Attorney, Agent, or Firm—Townsend & Banta

(57) ABSTRACT

A pack cosmetic which characteristically comprises dextrin. The present invention can provide an unprecedented superior pack cosmetic which gives high tension, adhesion, and a stretched feeling during use, is easy to remove, and can leave a superior moist feeling after removal. It can also provide a pack cosmetic which has a superior keratotic plug removal effect as well.

4 Claims, No Drawings

FACE PACK

This application is a 371 of PCT/JP98/05305 filed Nov. 25, 1998.

FIELD OF THE INVENTION

This invention relates in general to a pack cosmetic, and more particularly to a pack cosmetic containing dextrin as the main film agent which gives high levels of tension, adhesion, and a stretched feeling during use after drying; it not only gives a good feeling during use as a pack agent but also is easy to remove without straining the skin and leaves a moist feeling after removal.

BACKGROUND OF THE INVENTION

Conventionally, pack cosmetics can be largely divided into those which contain a large amount of humectants and oil for the purpose of moisture retention and activation of the skin and those which are given higher tension and adhesion during use for the purpose of cleansing.

Both types use, as the film agent, polyvinyl alcohol, vinyl acetate emulsion, xanthan gum, carboxyvinyl polymer, polyvinyl pyrolidone, and synthetic cellulose type polymer compounds.

However, the pack cosmetic which is given high tension and adhesion for the purpose of cleansing forms a film hardly soluble in water after drying and therefore strains the skin significantly when being peeled off and is not easy to remove, making it unsuitable for application on the whole face.

Also, the pack cosmetic which aims at moisture retention and activation does not form a strong film and therefore it does not give adequate tension and adhesion. There has not been any pack cosmetic which simultaneously gives moisture retention and activation effects as well as adequate tension and adhesion.

In view of the aforementioned situation, the inventors conducted earnest research to obtain a pack cosmetic which gives high tension, adhesion, and a stretched feeling during use and does not strain the skin when being peeled off, and discovered that a pack cosmetic which solves the aforementioned problem, i.e. gives adequate tension, adhesion, and a stretched feeling to the skin and is easy to peel off after use, giving a superior moist feeling, can be obtained by blending in dextrin as the main film agent in the pack base agent, thus completing the present invention.

The object of the present invention is to provide a new pack cosmetic which gives high tension, adhesion, and a stretched feeling during use, is easy to remove without straining the skin, and can give a superior moist feeling.

DISCLOSURE OF THE INVENTION

That is, the present invention provides a pack cosmetic which characteristically contains dextrin.

Also, the present invention provides the aforementioned pack cosmetic which additionally contains a polymer compound.

Furthermore, the present invention provides the aforementioned pack cosmetic wherein the aforementioned polymer compound is one or more substances selected from a group consisting of polyvinyl acetate, polyethyl acrylate, polyvinyl pyrolidone, polyvinylmethyl ether, alkanolamine polyacrylate, and vinyl pyrolidone-vinyl acetate copolymer.

Also, the present invention provides the aforementioned pack cosmetic which additionally contains an alcohol.

Furthermore, the present invention provides the aforementioned pack cosmetic which additionally contains a powder.

Also, the present invention provides the aforementioned pack cosmetic which additionally contains oil and a surfactant.

Furthermore, the present invention provides the aforementioned pack cosmetic wherein said pack cosmetic is a peel-off, wipe-off, or rinse-off type pack cosmetic.

THE BEST MODES OF THE EMBODIMENTS

The configuration of the present invention is described in detail below.

The dextrin for use in the present invention refers to the intermediate products of the process of hydrolyzing starch to maltose. They are represented by the general formula $(C_6H_{10}O_5)n.xH_2O$ and obtained by treating starch with enzymes, acid, heat, etc.

There are various types of dextrin depending on the method of hydrolysis. Examples include soluble starch, thin-glue starch, amylodextrin, white dextrin, yellow dextrin, erythrodextrin, and achrodextrin. Any one or more of them can be selected for use. For example, a water soluble mixture with various molecular weights can be used which is prepared by obtaining crude dextrin through a heating treatment, hydrolysis with acid, or hydrolysis with diastase of starch, dissolving it in water, followed by purification by means of precipitation using alcohol. Commercial products can be used.

The blend ratio of the dextrin in the pack cosmetic is preferably 0.5–25 wt %, more preferably 3.0–20 wt %, the most preferably 10–15 wt %, of the total pack cosmetic. If it is less than 0.5 wt % then adequate tension, adhesion, and a stretched feeling on the skin may not be achieved. If it is more than 25 wt % then there may be stability problems in that gelation occurs over time, discoloration occurs at high temperatures, etc.

It is preferable that the pack cosmetic of the present invention contain a polymer compound in addition to the aforementioned essential ingredients. Combined use with the polymer compound allows even higher tension, adhesion, and stretched feeling on the skin and increases the viscosity of the pack cosmetic to facilitate the application. This also has the effect of removing keratotic plugs.

The polymer compound used in the present invention is one of those which can be blended into the pack cosmetic in the form of an emulsion polymer or water soluble polymer. For the emulsion polymer, preferable are polyvinyl acetate and polyethyl acrylate. For the water soluble polymer, preferable are polyvinyl alcohol, polyvinyl pyrolidone, polyvinylmethyl ether, alkanolamine polyacrylate, vinyl pyrolidone-vinyl acetate copolymer, gum arabic, gelatin, methyl cellulose, ethyl cellulose, hydroxyethyl cellulose, sodium carboxymethyl cellulose, sodium arginate, alkyl methacrylate-dimethylaminoethyl methacrylate copolymer, polymethacryloyloxytrimethyl ammonium, and poly-2-acrylamide-2-methylpropanesulfonic acid. Particularly preferable examples in terms of both usability, such as giving a stretched feeling, and removal of keratotic plugs include polyvinyl acetate, polyethyl acrylate, polyvinyl pyrolidone, polyvinylmethyl ether, alkanolamine polyacrylate, and vinyl pyrolidone-vinyl acetate copolymer.

One or more of these polymer compounds can be selected for blending in. The blend ratio is preferably 0.1–10 wt % of the total pack cosmetic.

In addition to the aforementioned essential ingredients, it is preferable to blend an alcohol into the pack cosmetic of the present invention. Combined use with an alcohol allows even higher tension, adhesion, and stretched feeling on the skin and has the effect of accelerating the drying process after application of the pack cosmetic.

The alcohol used in the present invention is a lower alcohol, preferably ethanol or isopropanol. The blend ratio is preferably 1–30 wt % of the total pack cosmetic.

In addition to the aforementioned essential ingredients, it is preferable to blend a powder into the pack cosmetic of the present invention. Combined use with a powder allows even higher tension, adhesion, and stretched feeling on the skin and has the effect of accelerating the drying process after application of the pack cosmetic.

For use as the powder in the present invention, the mica type, the talc type, resin powder (including those which are spherical), silica, etc. are preferably used. One or more of these can be selected for blending in. The blend ratio is preferably 0.1–20 wt %.

In the present invention, oils and surfactants can be blended in addition to the aforementioned ingredients to further improve usability. The addition of an oil and a surfactant significantly improves the spreading during application on the skin, improves the moist feeling after use, and provides a pack cosmetic with a very smooth feeling.

The oil used in the present invention is not limited in particular, and any oil which is used in cosmetics can be used. Examples include natural animal/plant oils/fats such as macadamia nut oil, evening primrose oil, olive oil, mink oil, jojoba oil, lanolin, and squalene; hydrocarbons such as liquid petrolatum, squalane, and petrolatum; higher alcohols such as cetanol, stearyl alcohol, and cetyl alcohol; higher fatty acids such as myristic acid, palmitic acid, stearic acid, behenic acid, isostearic acid, oleic acid, linolic acid, linolenic acid, and oxystearic acid; esters such as pentaerythritol tetra 2-ethylhexanoate, isopropylmyristic acid, isopropylpalmitic acid, isopropylstearic acid, and glyceryl 2-ethylhexanoate; diorgano polysiloxanes with low to high viscosity such as dimethyl polysiloxane, methylphenyl polysiloxane, methylhydrogen polysiloxane and dimethyl siloxane/methylphenyl siloxane copolymer, cyclic siloxanes such as octamethylcyclotetrasiloxane, decamethylcyclopentasiloxane and tetramethyltetraphenyltetracyclosiloxane, cyclic siloxane solutions such as high polymer gum-like dimethyl polysiloxane, gum-like dimethylsiloxane/methylphenylsiloxane copolymer and gum-like dimethyl polysiloxane, diorgano polysiloxane containing alkyl groups with a carbon number of 6–50, and silicone oils such as amino modified silicone, alkyl modified silicone and fluorine modified silicone. One or more of these oils can be blended in. Using volatile silicone oil is preferable in terms of the sensation at the time of application. It is also possible to give a moist feeling to the skin after peeling by adding natural animal/plant oils/fats.

The blend ratio of the oil is 0.1–40 wt % of the total pack cosmetic. If it is less than 0.1 wt %, then the smooth feeling is insufficient. If it is more than 40 wt %, then stickiness may arise after use. A preferable range is 0.3–30 wt %, more preferably 1.0–20 wt %.

The selection of the surfactant for use in the present invention is not limited in particular, and surfactants which are normally blended into cosmetics can be used. For example, lipophilic non-ionic surfactants, hydrophilic non-ionic surfactants, anionic surfactants, cationic surfactants, and ampholytic surfactants can be used. Specific examples are listed below.

Examples of the lipophilic non-ionic surfactant include sorbitan fatty acid esters including sorbitan monooleate, sorbitan monoisostearate, sorbitan monolaurate, sorbitan monopalmitate, sorbitan monostearate, sorbitan sesquioleate, sorbitan trioleate, diglycerolsorbitan penta-2-ethylhexylate, and diglycerolsorbitan tetra-2-ethylhexylate, glycerine polyglycerine fatty acids including mono-cottonseed-fatty acid glyceryl ester, glyceryl monoerucate, glyceryl sesquioleate, glyceryl monostearate, glyceryl α, α'-oleate pyroglutamate and glyceryl monostearate monomalate, propylene glycol fatty acid esters including propylene glycol monostearate, as well as hydrogenated castor oil derivatives, and glycerol alkyl ether.

Examples of the hydrophilic non-ionic surfactant include POE sorbitan fatty acid esters including POE-sorbitan monooleate, POE-sorbitan monostearate, POE-sorbitan monooleate and POE-sorbitan tetraoleate, POE-sorbitol fatty acid esters including POE-sorbitol monolaurate, POE-sorbitol monooleate, POE-sorbitol pentaoleate and POE-sorbitol monostearate, POE-glycerol fatty acid esters including POE-glyceryl monostearate, POE-glyceryl monoisostearate and POE-glyceryl triisostearate, POE fatty acid esters including POE monooleate, POE distearate, POE monodioleate and ethylene glycol distearate; POE alkyl ethers including POE lauryl ether, POE oleyl ether, POE stearyl ether, POE behenyl ether, POE2-octyldodecyl ether and POE cholestanol ether, pluaronics including pluronic, POE-POP alkyl ethers including POE-POP cetyl ether, POE-POP2-decyltetradecyl ether, POE-POP monobutyl ether, POE-POP hydrogenated lanolin and POE-POP glycerol ether, tetra POE-tetra POP ethylenediamine condensates including tetronic, POE castor oil hydrogenated castor oil derivatives including POE castor oil, POE hydrogenated castor oil, POE hydrogenated castor oil monoisostearate, POE hydrogenated castor oil triisostearate, POE hydrogenated castor oil monopyroglutamate monoisostearate, and POE hydrogenated castor oil maleate, alkanol amides including coconut fatty acid diethanol amide, lauric acid monoethanol amide and fatty acid isopropanol amide; as well as POE propylene glycol fatty acid ester, POE alkyl amine, POE fatty acid amide, sucrose fatty acid ester, POE nonylphenylformaldehyde condensate, alkylethoxydimethylamine oxide and trioleyl phosphate.

Examples of the anionic surfactant include fatty acid soaps including soap base, sodium laurate and sodium palmitate, higher alkylsulfuric ester salts including sodium laurylsulfate and potassium laurylsulfate, alkyl ether sulfuric ester salts including triethanolamine POE laurylsulfate and sodium POE laurylsulfate, N-acylsarcosinic acids including sodium lauroylsarcosinate, higher fatty acid amide sulfonates including sodium N-myristoyl-N-methyltaurate, sodium methyltaurate cocoate and sodium laurylmethyltaurid, phosphoric ester salts including sodium POE oleyl ether phosphate and POE stearyl ether phosphoric acid, sulfosuccinates including sodium di-2-ethylhexylsulfosuccinate, sodium monolauroylmonoethanolamide polyoxyethylenesulfosuccinate and sodium laurylpolypropylene glycol sulfosuccinate, alkylbenzenesulfonates including sodium linear dodecylbenzenesulfonate, triethanolamine linear dodecylbenzenesulfonate and linear dodecylbenzenesulfonic acid, N-acylglutamates including monosodium N-lauroylglutamate, disodium N-stearoylglutamate and monosodium N-myristoyl-L-glutamate, higher fatty acid ester sulfates including sodium hydrogenated glyceryl cocoate sulfate, sulfated oils including turkey red oil, as well as POE alkyl ether carboxylate, POE alkylaryl ether carboxylate, α-olefinsulfonates, higher fatty acid ester sulfonate, sec-alcohol sulfate, higher fatty acid alkyloyl amide sulfate, sodium lauroyl monoethanolamine succinate, ditriethanolamine N-palmitoylaspartate and sodium caseinate.

Examples of the cationic surfactant include alkyltrimethyl ammonium salts including stearyltrimethyl ammonium chloride and lauryltrimethyl ammonium chloride, distearyl dimethyl ammonium chloride/dialkyl dimethyl ammonium chloride, alkylpyridinium salts including poly (N,N-dimethyl-3,5-methylene piperidine chloride) and cetyl pyridinium chloride, as well as alkyl quarternary ammonium salt, alkyldimethylbenzyl ammonium salt, alkylisoquinolinium salt, dialkylmorpholine salt, POE alkylamine, alkylamine salt, polyamine fatty acid derivatives, amylalcohol fatty acid derivatives, benzalkonium chloride and benzetonium chloride.

Examples of the ampholytic surfactant include imidazoline type ampholytic surfactants including 2-undecyl-N,N,N-(hydroxyethylcarboxymethyl)-2-imidazoline sodium salt and 2-cocoyl-2-imidazaliniumhydroxide-1-carboxyethyloxy 2 sodium salt and betaine type surfactants including 2-heptadecyl-N-carboxymethyl-N-hydroxyethyl imidazolinium betaine, betaine lauryldimethylamino acetate, alkyl betaine, amide betaine and sulfobetaine.

The blend ratio of the surfactant is not limited in particular and can be decided at will. Usually, 10 wt % or less of the total pack cosmetic is blended in. A blend ratio over 10 wt % may cause stickiness.

Also, in the present invention, it is preferable to blend in an acrylic acid methacrylic acid alkyl polymer in view of long-term stability. Particularly when the formulation of the pack cosmetic is a gel composition, the addition of oil may affect the long term stability. However, a gel composition pack cosmetic which has superior long term stability can be obtained by adding an acrylic acid methacrylic acid alkyl polymer. The type of the acrylic acid methacrylic acid alkyl polymer is not limited in particular. For example, Pemulen TR-2 (from B.F. Goodrich company), which is commercially available, can be used.

In addition to the aforementioned essential ingredients, the pack cosmetic of the present invention can contain, as necessary, ingredients commonly blended into a pack cosmetic within the range which does not affect the effect of the present invention. For example, other film agents, polyhydric alcohols, preservatives, disinfectants, ultraviolet absorbents, chelating agents, antioxidants, and perfumes can be blended in and the pack cosmetic can be manufactured according to a conventional method for any formulation.

The pack cosmetic of the present invention is a cosmetic which is widely used for the purpose of moisture retention and cleansing of the skin. Depending on how it is used, there are several types such as the peel-off type, wipe-off or rinse-off type, and pasting type. The way of the pack cosmetic of the present invention should be used is not limited in particular, but it should preferably be used as the wipe-off or rinse-off type pack cosmetic because it can be easily dissolved and removed by adding water.

EXAMPLES

The present invention is described in detail by referring to examples below. The present invention is not limited to these examples. The blend ratios in the examples are indicated in weight percent units.

Emulsion-type pack cosmetics of Examples and Comparative examples were prepared with the formulations shown in Table 1. Usability was evaluated by a panel of ten evaluation specialists according to the following evaluation method. Also, each pack cosmetic was stored at temperatures of −10° C., 0° C., room temperature (RT), 37° C., and 50° C., and four weeks later the stability was evaluated with the following evaluating method based on change of appearance and viscosity. The results are also shown in Table 1.

Method for Evaluating Usability

⊚: Nine or more out of ten reported that the tension, adhesion, and stretched feeling were very clear, removal was easy, and there was a moist feeling after the removal.
○: Six or more and eight or less out often reported that the tension, adhesion, and stretched feeling were very clear, removal was easy, and there was a moist feeling after the removal.
Δ: Three or more and five or less out often reported that the tension, adhesion, and stretched feeling were very clear, removal was easy, and there was a moist feeling after the removal.
X: Two or less out often reported that the tension, adhesion, and stretched feeling were very clear, removal was easy, and there was a moist feeling after the removal.

Stability Evaluation Method

⊚: After four weeks, no change was observed under any of the temperature conditions.
○: After four weeks, a small change was observed at −10° C. or 50° C., but the degree of the change was within the acceptable limit.
Δ: After four weeks, a change was observed at −10° C. or 50° C., and the degree of the change was outside of the acceptable limit.
X: After four weeks, a change was observed under all of the temperature conditions, and the degree of the change was outside of the acceptable limit.

Examples 1–7 and Comparative Examples 1–3

Preparation Method (2)–(5) in Table 1 were added to (1) and homogeneously stirred. (7), dissolved in (6), was then added to this while stirring until the mixture was homogeneous to obtain a pack cosmetic. The dextrin used was a pharmacopoeia entry.

TABLE 1

|  | Comparative example 1 | Example 1 | Example 2 | Example 3 | Example 4 |
|---|---|---|---|---|---|
| (1) Ion exchanged water | 94.28 | 93.28 | 91.28 | 84.28 | 79.28 |
| (2) Dextrin | 0.0 | 1.0 | 3.0 | 10.0 | 15.0 |
| (3) Carboxyvinyl polymer | 0.5 | 0 | 0.5 | 0.5 | 0.5 |
| (4) Carboxymethyl cellulose | 0.1 | 0.1 | 0.1 | 0.1 | 0.1 |
| (5) Caustic potash | 0.02 | 0.02 | 0.02 | 0.02 | 0.02 |
| (6) Ethyl alcohol | 5.0 | 5.0 | 5.0 | 5.0 | 5.0 |
| (7) Methyl paraben | 0.1 | 0.1 | 0.1 | 0.1 | 0.1 |
| Usability | X | ○ | ⊚ | ⊚ | ⊚ |

TABLE 1-continued

| Stability | ⊚ | ⊚ | ⊚ | ⊚ | ⊚ |
|---|---|---|---|---|---|
| | Comparative example 2 | Example 5 | Example 6 | Example 7 | Comparative example 3 |
| (1) Ion exchanged water | 79.28 | 74.28 | 69.28 | 64.28 | 64.28 |
| (2) Dextrin | 0.0 | 20.0 | 25.0 | 30.0 | 0.0 |
| (3) Polyvinyl alcohol | 15.5 | 0.5 | 0.5 | 0.5 | 30.5 |
| (4) Carboxymethyl cellulose | 0.1 | 0.1 | 0.1 | 0.1 | 0.1 |
| (5) Caustic potash | 0.02 | 0.02 | 0.02 | 0.02 | 0.02 |
| (6) Ethyl alcohol | 5.0 | 5.0 | 5.0 | 5.0 | 5.0 |
| (7) Methyl paraben | 0.1 | 0.1 | 0.1 | 0.1 | 0.1 |
| Usability | Δ | ⊚ | ⊚ | ⊚ | X |
| Stability | ○ | ○ | Δ | X | X |

As shown in Table 1, the pack cosmetics of the present invention containing dextrin have superior usability. Those with higher dextrin contents tend to have inferior stability.

The pack cosmetics shown in Table 2 were prepared by a conventional method and an actual-use test was conducted by a panel of 20 women for evaluation. For the peel-off type, the cosmetic was directly applied on the skin. For the sheet type, an appropriate amount of tap water was applied on the nose area of a panelist, and then a 3×7 cm rectangular sample was pasted on and, after letting stand for drying, peeled off. In this panel test, the keratotic plug removal, pain at the time of peeling, usability (stickiness), and drying properties were evaluated according to the following criteria. The results are also shown in Table 2.

Evaluation Criteria

⊚: 18 or more out of 20 evaluated the sample as good.
○: 15 or more and 17 or less out of 20 evaluated the sample as good.
Δ: 10 or more and 14 or less out of 20 evaluated the sample as good.
X: Less than 10 out of 20 evaluated the sample as good.

TABLE 2

Peel-off pack cosmetic: Examples 8–11, Comparative examples 4, 5

| | Comparative example 4 | Example 8 | Example 9 | Example 10 | Example 11 | Comparative example 5 |
|---|---|---|---|---|---|---|
| A. Water phase | | | | | | |
| Ion exchanged water | 74.75 | 74.6 | 72.8 | 68.8 | 58.8 | 52.8 |
| Dipropylene glycol | 5.0 | 5.0 | 5.0 | 5.0 | 5.0 | 5.0 |
| Polyvinyl alcohol (molecular weight: 100,000) | 15.0 | 15.0 | 15.0 | 15.0 | 15.0 | 15.0 |
| Dextrin | 0 | 0.2 | 2.0 | 6.0 | 16.0 | 22.0 |

TABLE 2-continued

Peel-off pack cosmetic: Examples 8–11, Comparative examples 4, 5

| | Comparative example 4 | Example 8 | Example 9 | Example 10 | Example 11 | Comparative example 5 |
|---|---|---|---|---|---|---|
| B. Alcohol phase | | | | | | |
| Methyl paraben | 0.1 | 0.1 | 0.1 | 0.1 | 0.1 | 0.1 |
| Ethanol | 5.0 | 5.0 | 5.0 | 5.0 | 5.0 | 5.0 |
| Perfume | 0.1 | 0.1 | 0.1 | 0.1 | 0.1 | 0.1 |
| Keratotic plug removal | X | ○ | ⊚ | ⊚ | ⊚ | ⊚ |
| Pain at the time of peeling | Δ | ○ | ⊚ | ⊚ | ⊚ | ⊚ |
| Feeling during use (stickiness) | ⊚ | ⊚ | ⊚ | ⊚ | ○ | X |
| Drying properties | ○ | ○ | ○ | ○ | ○ | ○ |

Preparation Method

The water phase A was heated up to 80° C., stirred and dissolved, and cooled down to room temperature, to which the ethanol phase B, stirred and dissolved in a separate container, was added and homogeneously mixed to obtain the pack cosmetic.

As clearly shown in Table 2, the keratotic plug removal is not sufficient and there is pain at the time of peeling off if the blend ratio of dextin is less than 0.1 wt %. A blend ratio over 20 wt % is not preferable because then it feels sticky during use. Therefore, a preferable dextrin content is 0.1–20 wt %, more preferably 0.5–15 wt %.

Using the formulations shown in Table 3 and Table 4, emulsion type rinse-off type pack cosmetics were prepared and their usability was evaluated with an actual use test by a panel of ten evaluation specialists according to the following evaluation criteria. Also, each pack cosmetic was stored at temperatures of −10° C., 0° C., room temperature (RT), 37° C., and 50° C., and four weeks later the stability was evaluated with the following evaluating method based on change of appearance and viscosity. The results are also shown in Table 3 and Table 4.

Usability Evaluation Criteria

⊚: Nine or more out of ten reported that the spread during use, smooth feeling after use, and stretched feeling after use were all good.
○: Six or more and eight or less out of ten reported that the spread during use, smooth feeling after use, and stretched feeling after use were all good.
Δ: Three or more and five or less out of ten reported that the spread during use, smooth feeling after use, and stretched feeling after use were all good.
X: Two or less out of ten reported that the spread during use, smooth feeling after use, and stretched feeling after use were all good.

Stability Evaluation Method

⊚: After four weeks, no change was observed under any of the temperature conditions.
○: After four weeks, a small change was observed at −10C or 50° C., but the degree of the change was within the acceptable limit.

Δ: After four weeks, a change was observed at −10° C. or 50° C., and the degree of the change was outside of the acceptable limit.

X: After four weeks, a change was observed under all of the temperature conditions, and the degree of the change was outside of the acceptable limit.

TABLE 3

|  | Example 12 | Example 13 | Example 14 | Example 15 |
|---|---|---|---|---|
| (1) Ion exchanged water | Balance | Balance | Balance | Balance |
| (2) Dextrin | 2.0 | 2.0 | 2.0 | 2.0 |
| (3) Carboxymethyl cellulose | 0.4 | 0.4 | 0.4 | 0.4 |
| (4) 1,3-butylene glycol | 2.0 | 2.0 | 2.0 | 2.0 |
| (5) Gum arabic | 0.3 | 0.3 | 0.3 | 0.3 |
| (6) Methyl polysiloxane | 0 | 0.1 | 1.0 | 5.0 |
| (7) Polyoxyethylene (15 mole) oleyl ether | 0 | 0.1 | 0.1 | 0.1 |
| (8) Acrylic acid methacrylic acid alkyl polymer (Pemulen TR-2 from B. F. Goodrich company) | 0 | 0.05 | 0 | 0.05 |
| (9) Ethyl alcohol | 10.0 | 10.0 | 10.0 | 10.0 |
| (10) Caustic potash | 0.04 | 0.04 | 0.04 | 0.04 |
| (11) Methyl paraben | 0.1 | 0.1 | 0.1 | 0.1 |
| Usability |  |  |  |  |
| Spread | ○ | ◎ | ◎ | ◎ |
| Smooth feeling | Δ | ○ | ◎ | ◎ |
| Stretched feeling | ◎ | ◎ | ◎ | ◎ |
| Stability | ○ | ◎ | ◎ | ◎ |

TABLE 4

|  | Example 16 | Example 17 | Example 18 | Example 19 |
|---|---|---|---|---|
| (1) Ion exchanged water | Balance | Balance | Balance | Balance |
| (2) Dextrin | 2.0 | 2.0 | 2.0 | 2.0 |
| (3) Carboxymethyl cellulose | 0.4 | 0.4 | 0.4 | 0.4 |
| (4) 1,3-butylene glycol | 2.0 | 2.0 | 2.0 | 2.0 |
| (5) Gum arabic | 0.3 | 0.3 | 0.3 | 0.3 |
| (6) Methyl polysiloxane | 10.0 | 20.0 | 35.0 | 35.0 |
| (7) Polyoxyethylene (15 mole) oleyl ether | 0.1 | 0.1 | 0.1 | 0.1 |
| (8) Acrylic acid methacrylic acid alkyl polymer (Pemulen TR-2 from B. F. Goodrich company) | 0.05 | 0.1 | 0.1 | 0 |
| (9) Ethyl alcohol | 10.0 | 10.0 | 10.0 | 10.0 |
| (10) Caustic potash | 0.04 | 0.04 | 0.04 | 0.04 |
| (11) Methyl paraben | 0.1 | 0.1 | 0.1 | 0.1 |
| Usability |  |  |  |  |
| Spread | ○ | ◎ | ◎ | ○ |
| Smooth feeling | ◎ | ◎ | ○ | ○ |
| Stretched feeling | ◎ | ◎ | ○ | Δ |
| Stability | Δ | ◎ | ◎ | Δ |

Table 3 and Table 4 indicate that the addition of the oil ingredient, methyl polysiloxane, improves usability (the smooth feeling), and that the best usability is achieved when the oil content is 1.0–20.0 wt %. These tables also indicate that the addition of an acrylic acid methacrylic acid alkyl polymer improves usability (spread) and stability.

Examples of the present invention are shown below.

Example 20

Rinse-off Type Pack Cosmetic

| (1) Ion exchanged water | 56.17 wt % |
|---|---|
| (2) Dextrin | 15.0 |
| (3) Xanthan gum | 0.2 |
| (4) Carboxymethyl cellulose | 0.2 |
| (5) Silica | 1.0 |
| (6) Dipropylene glycol | 5.0 |
| (7) Sodium metaphosphate | 0.03 |
| (8) L-arginine | 0.3 |
| (9) Ethyl alcohol | 20.0 |
| (10) Isopropyl alcohol | 2.0 |
| (11) Methyl paraben | 0.1 |

Preparation Method (2)–(8) were added to (1) and homogeneously stirred and then, while stirring, (9)–(10) and (11) were added and mixed homogeneously to obtain the pack cosmetic of the present invention. The obtained pack cosmetic had superior usability and good temperature stability.

Example 21

Emulsion Rinse-off Type Pack Cosmetic

| (1) Ion exchanged water | 66.4 wt % |
|---|---|
| (2) Trehalose | 1.0 |
| (3) Dextrin | 15.0 |
| (4) Polyvinyl alcohol | 3.0 |
| (5) Hydroxypropylmethyl cellulose | 2.0 |
| (6) Glycerine | 3.0 |
| (7) Dipropylene glycol | 5.0 |
| (8) Polyoxyethylene (20 mole) behenyl ether | 0.5 |
| (9) Olive oil | 1.0 |
| (10) Decamethylcyclopentasiloxane | 2.0 |
| (11) Methyl paraben | 0.1 |

Preparation Method (2)–(7) and (11) were added to (1) and homogeneously stirred and then, while stirring, (8)–(10) were added and mixed homogeneously to obtain the pack cosmetic of the present invention. The obtained pack cosmetic had superior usability and good temperature stability.

Example 22

Emulsion Rinse-off Type Pack Cosmetic

| (1) Ion exchanged water | 85.85 wt % |
|---|---|
| (2) Dextrin | 5.0 |
| (3) Hydroxyethyl cellulose | 1.0 |
| (4) Polyoxyethylene (30 mole) stearic ester | 0.5 |
| (5) Potassium stearate | 0.5 |
| (6) High polymer methyl polysiloxane (2)-methyl polysiloxane solution (20%) | 2.0 |
| (7) Octamethylcyclopentasiloxane | 5.0 |
| (8) Methyl paraben | 0.15 |

Preparation Method (1)–(3) and (8) were mixed and homogeneously stirred and then, while stirring, (4)–(7) were added and mixed homogeneously to obtain the pack cosmetic of the present invention. The obtained pack cosmetic had superior usability and good temperature stability.

Example 23

Emulsion Rinse-off Type Pack Cosmetic

| | |
|---|---|
| (1) Ion exchanged water | 80.65 wt % |
| (2) Dextrin | 8.0 |
| (3) Polyvinylmethyl ether | 0.3 |
| (4) Xanthan gum | 2.0 |
| (5) 1,3-butylene glycol | 5.0 |
| (6) Polyoxyethylene (60 mole) hydrogenated castor oil | 0.5 |
| (7) Squalane | 2.0 |
| (8) Tocopherol acetate | 0.05 |

Preparation Method (1)–(5) were mixed and homogeneously stirred and then, while stirring, (6)–(8) were added and mixed homogeneously to obtain the pack cosmetic of the present invention. The obtained pack cosmetic had superior usability and good temperature stability.

Example 24

Emulsion Rinse-off Type Pack Cosmetic

| | |
|---|---|
| (1) Ion exchanged water | 75.78 wt % |
| (2) Dextrin | 1.0 |
| (3) Carboxymethyl cellulose | 0.2 |
| (4) Hydroxyethyl cellulose | 1.0 |
| (5) Erythritol | 3.0 |
| (6) Dipropylene glycol | 5.0 |
| (7) Acrylic acid methacrylic acid alkyl copolymer (Pemulen TR-2 from B. F. Goodrich company) | 1.0 |
| (8) Methylphenyl polysiloxane | 3.0 |
| (9) Decamethylcyclopentasiloxane | 5.0 |
| (10) Vitamin A palmitate | 0.1 |

Preparation Method (1)–(6) were mixed and homogeneously stirred and then, while stirring, (7)–(10) were added and mixed homogeneously to obtain the pack cosmetic of the present invention. The obtained pack cosmetic had superior usability and good temperature stability.

Industrial Applicability of the Invention

The present invention can provide an unprecedented superior pack cosmetic which gives high tension, adhesion, and a stretched feeling during use, is easy to remove, and leaves a moist feeling after removal. It can also provide a pack cosmetic which has a superior keratotic plug removal effect as well.

What is claimed is:

1. A wipe-off aqueous emulsion pack cosmetic consisting essentially of:

water;

0.5–25 wt % dextrin;

1–30 wt % ethanol or isopropanol;

0.1–20 wt % powder;

1–40 wt % oil, and optionally 10 wt % or less surfactant.

2. The wipe-off aqueous emulsion pack cosmetic of claim 1 which further comprises about 0.1–0.6 wt % of a viscosity increasing agent selected from the group consisting of the polyvinyl alcohol, polyvinyl pyrolidone, poltyvinylmethyl ether, alkanolamine polyacrylate, vinyl pyrolidone-vinyl acetate copolymer, gum arabic, gelatin, methyl cellulose, ethyl cellulose, hydroxyethyl cellulose, sodium carboxymethyl cellulose, sodium arginate, alkyl methacrylate-dimethylaminoethyl methacrylate copolymer, polymethacryloyloxytrimethyl ammonium, poly-2-acrylamide-2-methylpropanesulfonic acid, polyvinyl acetate, and polyethyl acrylate.

3. A wipe-off aqueous emulsion pack cosmetic comprising:

(a) 0.25–25 wt % dextrin;

(b) about 0.1–0.6 wt % of a polymer;

(c) alcohol;

(d) powder;

(e) oil;

(f) surfactant; and (g) water.

4. A method of treating the skin with a wipe-off aqueous emulsion pack cosmetic to provide high tension, adhesion, and stretch feeling during use, which can be removed without straining the skin and which provides a superior moist feeling, comprising:

(a) applying to the skin the composition of claim 3, (b) drying said composition, and (c) then wiping off resultant dried composition.

* * * * *